United States Patent [19]

Papenfuhs

[11] 4,052,438

[45] Oct. 4, 1977

[54] PROCESS FOR PREPARING AROMATIC HYDROXY-CARBOXYLIC ACID ALKYL ESTERS

[75] Inventor: Theodor Papenfuhs, Frankfurt am Main, Germany

[73] Assignee: Hoechst Aktiengesellschaft, Frankfurt am Main, Germany

[21] Appl. No.: 549,173

[22] Filed: Feb. 12, 1975

[30] Foreign Application Priority Data

Feb. 15, 1974 Germany .............................. 2407187

[51] Int. Cl.$^2$ ............................................. C07C 69/76
[52] U.S. Cl. .................................. 560/61; 260/347.5; 560/56
[58] Field of Search ........................ 260/473 S, 473 F

[56] References Cited
PUBLICATIONS

Roberts & Caserio, Basic Principles of Organic Chem.

*Primary Examiner*—Paul J. Killos
*Attorney, Agent, or Firm*—Connolly and Hutz

[57] ABSTRACT

An improved process for the preparation of aromatic hydroxycarboxylic acid alkyl esters had been found which avoids working with organic solvents and especially avoids the formation of alkyl ether compounds by reaction of the dialkyl sulfate with the phenolic hydroxy groups. The final products are obtained in a high selectivity and with high yields. The novel process is carried out by esterification of an aromatic hydroxycarboxylic acid with a dialkylsulfate in an aqueous medium at a pH-value in the range of from about 4 to 6.5, preferably at a temperature in the range of from 40° to 80° C, and it may advantageously be used as a subsequent reaction of a technically suitable carboxylation process of aromatic hydroxy compounds by esterification of its aromatic hydroxy-carboxylic acid final compounds.

3 Claims, No Drawings

PROCESS FOR PREPARING AROMATIC HYDROXY-CARBOXYLIC ACID ALKYL ESTERS

The present invention relates to an improved process for preparing aromatic hydroxy-carboxylic acid alkyl esters by esterification of aromatic hydroxy-carboxylic acids with dialkyl-sulfates in an aqueous medium.

It is already known to esterify aromatic hydroxy-carboxylic acids with dialkyl-sulfates, especially dimethyl sulfate, in an aqueous medium (cf. Houben-Weyl, Methoden der organischen Chemie, volume 8 (1952), pages 542 and 543, and Berichte der deutschen Chemischen Gesellschaft, volume 37 (1904), pages 3658 to 3661).

For this purpose the carboxylic acids are converted first into their alkali salts and then reacted with dimethyl sulfate. However, according to this process there is not obtained the hydroxy-carboxylic acid alkyl esters, but largely the alkoxycarboxylic acid alkyl esters, for example if dimethyl sulfate and hydroxy-naphthoic acid are used, the methoxy-naphthoic acid methyl ester is, thus, obtained.

The portion of alkoxy ester can no longer be split back into the desired hydroxy ester under technically reasonable reaction conditions and therefore gets lost; thus, the resulting yields are completely unsatisfying so that it is quite natural not to use this reaction on an industrial scale.

Aromatic hydroxy-carboxylic acid alkyl esters are, however, very requested products used i.a. as conservation ingredients, anti-light agents, dyestuff intermediate products and dyestuff auxiliaries.

Their preparation on an industrial scale is exclusively effected by esterifying the free hydroxy-carboxylic acid with the addition of mineral acid in alcohol in excess, which brings about an isolation of the starting product generally obtainable only by phenolate or naphtholate carboxylation, separation of the final product by filtration of the solvent as well as regeneration of the alcohol in excess.

Therefore, these processes requiring high expenditures of work and investment are, only to a limited extent, suitable for preparation on an industrial scale, so that a more favorable synthesis was desirable.

It is furthermore known how to prepare hydroxy-benzoic acid methyl esters by esterifying hydroxy-benzoic acid with dimethyl sulfate in acetone (cf. Chemical Abstract, Vol. 49 (1955), 11594 h). But this process is not suitable for use on an industrial scale, since, when operating in acetone or methanol the destruction of the dialkyl sulfate used in excess and the regeneration of the solvent cause considerable difficulties.

It has now been found that aromatic hydroxy-carboxylic acid alkyl esters, especially those having an alkyl ester group of 1 to 5 carbon atoms, are obtained with a high selectivity and yield, if the esterification of aromatic hydroxy-carboxylic acids is effected with dialkyl sulfates in an aqueous medium at a pH-value of about 4 to 6.5.

There are preferably prepared compounds corresponding to the formula

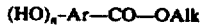

(HO)$_n$-Ar-CO-OAlk wherein Ar is a phenylene group or a phenylene substituted by a lower alkyl group, preferably a methyl group or napththylene radical, Alk is the methyl or ethyl radical and $n$ is the number 1 or 2.

The process is expediently carried out by adjusting the aqueous solution of the alkali salt of the aromatic hydroxycarboxylic acid to a pH-value of about 4 to 6.5, preferably about 5.0 to 5.5 with acid, preferably with a mineral acid such as hydrochloric or sulfuric acid, and subsequently esterifying by simultaneous addition of the dialkyl sulfate and an alkaline hydroxyde solution, while maintaining constant the pH-range adjusted, at temperatures between about 40° and 80° C, preferably between about 50° and 60° C.

Then the excess of the alkylating agent is destroyed by addition of ammonia and the final product is precipitated at a pH-value of about 7 to 8.5 with mineral acid, if desired after an intermediate clarification with charcoal and/or a clearing with a usual bleaching agent such as sodium dithionite, then it is filtered and dried.

Starting compounds for the process of the invention are for example phenol-carboxylic acids such as the salicylic acid or p-hydroxy-benzoic acid, dihydroxy-benzoic acids, naphtholcarboxylic acids, such as the 2-hydroxy-naphthalene-3-carboxylic acid, phenol-carboxylic acids containing lower alkyl or alkoxy groups, for example cresol-carboxylic acids and xylene-carboxylic acids, furthermore heterocyclic compounds such as hydroxycarbazol-carboxylic acids or hydroxy-dibenzofurane-carboxylic acids.

As dialkyl sulfates there are preferably used compounds easy to be prepared on an industrial scale, such as dimethyl sulfate and diethyl sulfate.

The process of the invention is particularly suitable as secondary, reaction following a carboxylation of an aromatic hydroxy compound, for example according to Kolbe-Schmitt or Marasse, which represent technically preferred process of preparation for the starting compounds. The carboxylate (alkali salt or the aromatic hydroxy-carboxylic acid) obtained as a reaction product and freed from phenol or naphthol used in excess is dissolved in water and esterified without intermediate isolation of the free acid after adjusting the pH-value corresponding to the process of the invention.

Thus, the novel process furthermore permits to convert a phenol or naphthol in a one-pot reaction directly into the corresponding aromatic hydroxy-carboxylic acid ester with an excellent yield and purity, avoiding, thus, regenerations, filtrations, drying and complicated apparatus. The considerable technical process resulting from this process is evident.

The following Example illustrates the invention. Parts are by weight.

EXAMPLE 1

650 Parts of an aqueous solution of the dipotassium salt of the p-hydroxy-benzoic acid containing 138 parts of the free p-hydroxy-benzoic acid, were introduced into a flask provided with a stirrer, thermometer, dropping funnels and a pH- electrode.

By introducing 100 parts of concentrated sulfuric acid the pH-value was adjusted to 5.0. After heating to 55° - 60° C 277 parts of dimethyl sulfate were added dropwise in the course of three hours at this temperature; by simultaneous addition of 200 parts of a 33% sodium hydroxide solution the pH-value was maintained at 6.0. Stirring was continued for 30 minutes successively 500 parts of water and 226 parts of a 25% ammonia were added, whereupon the crude p-hydroxy-benzoic acid methyl ester which had been precipitated during esterification, was dissolved. After adding 5 parts of charcoal the solution was stirred for 15 minutes and clarified over a suction-filter covered with 5 parts of kieselguhr; the filtrate was cleared with 0.5 part of sodium dithionite. Then 120 parts of concentrated sulfuric acid were introduced dropwise within 30 minutes, until a pH-value of 8.5 was obtained, stirring was continued for one hour while cooling to 20° C, the whole was suction-filtered, washed until neutral and dried.

About 137 parts (=90% of the theory) of p-hydroxybenzoic acid methyl ester having a melting point of 124° to 125° C were obtained.

The following Table contains further aromatic hydroxy-carboxylic acid alkyl esters obtained according to the invention, which have been prepared in analogous way to Example 1.

| Example No. | Compound | Yield | Melting Point |
|---|---|---|---|
| 2 | HO—⟨⟩—COOC₂H₅ | 92.5% | 115–116° C |
| 3 | COOCH₃ / OH (naphthalene) | 93.1% | 78–79° C |
| 4 | OH / COOCH₃ (naphthalene) | 95.6% | 74–75° C |
| 5 | OH / COOC₂H₅ (naphthalene) | 95.8% | 83–84° C |
| 6 | HO—⟨CH₃⟩—COOC₂H₅ | 86.9% | 98° C |
| 7 | OH / HO—⟨⟩—COOCH₃ | 88.8% | 117–118° C |
| 8 | OH / ⟨⟩—COOCH₃ | 91.0% | |
| 9 | OH / ⟨⟩—COOCH₃ / OH | 87.5% | 66–67° C |
| 10 | HO / ⟨⟩—COOC₂H₅ / HO | 90.4% | 127° C |
| 11 | HO—⟨naphthalene⟩—COOC₂H₅ | 94.8% | 110–112° C |
| 12 | OH / H₃C—⟨⟩—COOC₂H₅ | 87.0% | |

What is claimed is:

1. In a process for preparing an aromatic hydroxy-carboxylic acid alkyl ester by esterification of an aromatic hydroxy-carboxylic acid with a dialkyl sulfate in an aqueous medium, said ester and sulfate having 1–5 carbon atoms in the alkyl moiety, the improvement consisting of carrying out the esterification at a pH-value of about 4 to 6.5.

2. Process as claimed in claim 1, wherein said esterification is carried out at 40° to 80° C.

3. Process as claimed in claim 1, wherein said esterification is carried out after the carboxylation of aromatic hydroxy compounds.